United States Patent
Seitz et al.

(10) Patent No.: US 10,539,865 B2
(45) Date of Patent: Jan. 21, 2020

(54) METHOD AND DEVICE FOR DETERMINING AN OPC MODEL

(71) Applicant: Carl Zeiss SMT GmbH, Oberkochen (DE)

(72) Inventors: Holger Seitz, Jena (DE); Thomas Thaler, Jena (DE); Ute Buttgereit, Jena (DE); Thomas Trautzsch, Jena (DE)

(73) Assignee: Carl Zeiss SMT GmbH, Oberkochen (DE)

( * ) Notice: Subject to any disclaimer, the term of this patent is extended or adjusted under 35 U.S.C. 154(b) by 88 days.

(21) Appl. No.: 15/715,904

(22) Filed: Sep. 26, 2017

(65) Prior Publication Data

US 2018/0095358 A1 Apr. 5, 2018

(30) Foreign Application Priority Data

Sep. 30, 2016 (DE) .................. 10 2016 218 977

(51) Int. Cl.
*G06F 17/50* (2006.01)
*G03F 1/00* (2012.01)
(Continued)

(52) U.S. Cl.
CPC .............. *G03F 1/144* (2013.01); *G03F 1/36* (2013.01); *G03F 1/70* (2013.01); *G03F 7/70308* (2013.01);
(Continued)

(58) Field of Classification Search
CPC ......... G03F 1/144; G03F 1/36; G06F 7/70308
(Continued)

(56) References Cited

U.S. PATENT DOCUMENTS 7,027,143 B1 4/2006 Stokowski et al.
7,626,689 B2 12/2009 Stroessner et al.
(Continued)

FOREIGN PATENT DOCUMENTS

| DE | 10 2005 042 496 | 3/2007 | ............. G02B 27/58 |
| DE | 10 2005 062 237 | 7/2007 | ............... G03F 7/20 |
| DE | 10 2009 038 558 | 3/2011 | ............... G03F 7/20 |

OTHER PUBLICATIONS

German Office Action for German Application No. 10 2016 218 977.8 dated May 5, 2017.
(Continued)

*Primary Examiner* — Suchin Parihar
(74) *Attorney, Agent, or Firm* — Fish & Richardson P.C.

(57) ABSTRACT

A method is provided for determining an OPC model comprising: recording an aerial image by use of a mask inspection microscope, wherein the aerial image comprises at least one segment of a mask; simulating a plurality of aerial images which comprise at least the segment, proceeding from a mask design and from predefined parameters of an optical model which is part of the OPC model, wherein the parameters differ for each of the simulated aerial images of the plurality of aerial images; determining differences between the measured aerial image and the simulated aerial images; determining those parameters for which the differences between simulated aerial image and measured aerial image are the least.
In addition, a mask inspection microscope for carrying out the method is provided.

24 Claims, 2 Drawing Sheets

(51) Int. Cl.
*G03F 1/36* (2012.01)
*G03F 1/70* (2012.01)
*G03F 7/20* (2006.01)
*G01M 11/02* (2006.01)
*G01N 21/956* (2006.01)

(52) U.S. Cl.
CPC ....... *G01M 11/0285* (2013.01); *G01N 21/956* (2013.01); *G03F 7/70666* (2013.01)

(58) Field of Classification Search
USPC .......................................................... 716/53
See application file for complete search history.

(56) References Cited

U.S. PATENT DOCUMENTS

| 7,961,297 | B2 | 6/2011 | Greif-Wuestenbecker et al. |
| 2007/0061773 | A1* | 3/2007 | Ye ........................ G03F 7/70441 716/52 |
| 2007/0282574 | A1* | 12/2007 | Huang .................... G03F 7/705 703/2 |
| 2011/0090329 | A1 | 4/2011 | Poortinga et al. |
| 2011/0239169 | A1* | 9/2011 | Tirapu-Azpiroz ........ G03F 1/38 716/55 |
| 2013/0232454 | A1* | 9/2013 | Chou ........................ G03F 1/36 716/53 |
| 2014/0123084 | A1 | 5/2014 | Tang et al. |

OTHER PUBLICATIONS

H.H. Hopkins, "On the diffraction theory of optical images", Proceedings of the Royal Society of London. Series A, Mathematical and Physical Sciences, vol. 217, Issue 1130, pp. 408-432, (May 7, 1953).

M. Totzeck, "Numerical simulation of high-NA quantitative polarization microscopy and corresponding near-fields," Optik, vol. 112, No. 9, pp. 399-406 (2001).

* cited by examiner

METHOD AND DEVICE FOR DETERMINING AN OPC MODEL

CROSS-REFERENCE TO RELATED APPLICATION

Under 35 U.S.C. § 119, this application claims priority to German Patent Application 10 2016 218 977.8, filed on Sep. 30, 2016. The disclosure content of the above application is hereby incorporated by reference in its entirety.

TECHNICAL FIELD

This patent specification relates to a method for determining an OPC model.

This patent specification additionally relates to a mask inspection microscope for carrying out the method.

BACKGROUND

Photomasks, referred to for short as masks or else as reticles, are used in lithographic methods for chip production. Structures that serve for imaging desired structures on wafers are formed on said masks. Said structures on the mask are predefined as mask design. Lithographic scanners are used for the exposure of wafers. A light-sensitive layer, the resist, is formed on a wafer. Said resist is developed after exposure by the scanner and the structure is etched into the wafer surface.

Structures produced on the wafer are becoming smaller and smaller. In order to produce the structures, the resolution limit of the optical units used in scanners has to be exploited further and further. The optical unit of a scanner acts similar to a low-pass filter between mask and wafer. This low-pass filtering has the effect that structures on the mask mutually influence one another during the imaging. An imaging of a structure onto the wafer is influenced not only by itself but also by its neighborhood. The imaging quality is influenced by further mask properties such as, e.g.: Refractive index of the mask substrate, thickness of the absorber, side wall angle, corner rounding, dimensions of structure features such as, for example, changes in the line widths of structures, line end shortening.

Since the influences are attributable to optical effects and since they are locally delimited, these effects are referred to as optical proximity effects (OPC effects for short).

Besides the OPC effects mentioned, the mask structures on the way to the structure on the wafer are changed by further effects. These may be, for example: optical aberrations as a result of the optical system of the scanner, apodization and vector effects, effects during the exposure and development of the resist and during the etching of the wafer.

Nowadays, all factors which change the structure on a mask until the representation thereof on the wafer are referred to as OPC effects.

In order to counteract these undesired changes in the structures on the wafer, the structures on the mask are changed in a targeted manner such that the imaging of the changed structures with the effects brought about by the lithographic system produces a structure on the wafer which comes as close as possible to the desired structure. This correction of a mask is called Optical Proximity Correction (abbreviated to OPC).

The change experienced by a structure on a mask proceeding from a predefined mask design until the formation of a wafer structure is described in a so-called OPC model.

An OPC model has numerous parameters for adaption to the lithography process used. This adaptation is effected empirically by a calibration mask being fabricated, on which test structures are formed, which are exposed onto a wafer. The wafer structures produced in the process are measured by use of a wafer CD-SEM. With this information, the parameters of the OPC model are then adapted such that, proceeding from the known mask designs, they can determine the resulting wafer structures with high possible accuracy. The OPC models are implemented in commercially available software solutions, such as, for example, the Calibre or nmWorkFlow software from Mentor Graphics.

SUMMARY

Improvements can be made to the method described above for determining the descriptive parameters of the OPC model for the route from the mask to the wafer structure. For example, the OPC model described above is based merely on measurements of the final wafer structure. Consequently, the cause of changes in the structure can be determined only to a limited extent. It can be difficult to separate errors caused by optical effects from errors based on chemical effects. In this regard, it can happen, for example, that OPC effects that arise for example as a result of the imaging of the mask, i.e. errors which are already present in the aerial image, are corrected by changes in the resist model, or vice versa.

A general aspect of the invention is to provide a method and a mask inspection microscope which enable a highly accurate determination of an OPC model.

This aspect of the invention is achieved by use of a method for determining an OPC model that includes the following steps: recording an aerial image by use of a mask inspection microscope, wherein the aerial image comprises at least one segment of a mask; simulating a plurality of aerial images which comprise at least the segment, proceeding from a mask design and from predefined parameters of an optical model which is part of the OPC model, wherein the parameters differ for each of the simulated aerial images of the plurality of aerial images; determining differences between the measured aerial image and the simulated aerial images; and determining those parameters for which the differences between simulated aerial image and measured aerial image are the least.

Implementations of the invention can include one or more of the following features. The determination of parameters can be effected by way of an iteration, in which in each case from the differences between a measured aerial image and an aerial image determined by simulation, a change in the parameters is determined and these parameters are chosen as parameters of a following simulation. The OPC model can have at least one of an optical model or a resist model, in which the optical model includes at least one mask model or one scanner model. A calibration mask can be used as the mask. In a first step parameters of the mask model can be determined, in which the parameters of the mask model include at least one of the following parameters: complex material refractive indices, the refractive index of the mask substrate, thickness of the absorber, side wall angle, undercuts, corner rounding, change in the dimensions of structure features such as, for example, changes in the line widths of structures, or line end shortening. In a second step parameters of the scanner model can be determined, in which the parameters of the scanner model include at least one of the following parameters: Numerical aperture, stop, Jones pupil, or polarization. The method can further include recording an aerial image of a segment of a mask; simulating an aerial image on the basis of the mask design of the segment and of the OPC model determined; and comparing the measured aerial image and the simulated aerial image. The method can further include determining a measured wafer image by carrying out a wafer exposure and recording an image of the exposed wafer; determining a simulated aerial image of the at least one segment of the calibration mask using the optical model determined; determining a plurality of simulated wafer images on the basis of the measured aerial image; and of predefined parameters of the resist model; determining differences between the measured and the simulated wafer images; and determining the parameters for which the differences between the simulated wafer images and the measured wafer image are the least. The determination of parameters can be effected by way of an iteration, in which in each case from the differences between a measured wafer image and a wafer image determined by simulation, a change in the parameters is determined and these parameters are chosen as parameters of a following simulation. A resist model can be applied to a measured aerial image, in which the structure obtained is compared with the structure desired on the wafer, and the mask structure is correspondingly adapted on the basis of the differences. In each case a minimum, an optimum and a maximum value are predefined for the focus and for the exposure and wafer structures are determined for all 9 pairs of values.

The term OPC model denotes a model which describes the change experienced by a structure on a mask proceeding from a predefined mask design until the formation of a wafer structure. The term mask design denotes the two-dimensional structure predefined on a mask.

An OPC model can be divided into further models that can be applied step by step. An optical model describes the change in the mask design as far as an aerial image of the mask. Said aerial image is produced during the wafer exposure by the scanner in the resist.

A resist model describes the changes in the aerial image as a result of the resist, i.e. the production of a wafer structure from the aerial image. This model is also referred to as the chemical part of the OPC model.

Knowledge of these models makes it possible to determine error sources during the examination of masks. In other words, it is possible to ascertain whether the error resides in the optical or in the chemical part of the mask production process. A targeted error correction is thus made possible.

The optical model can be subdivided into a mask model and a scanner model.

The mask model describes the optical properties of a mask. The mask model comprises one or more mask parameters such as, for example, complex material refractive indices, the refractive index of the mask substrate, thickness of the absorber, side wall angle, undercuts, corner rounding, change in the dimensions of structure features such as, for example, changes in the line widths of structures, and line end shortening.

If the three-dimensional structure is also known in addition to the material properties of absorber and substrate of a mask model, a very precise simulation of aerial images is made possible. A rigorous simulation can then be carried out on the basis of the mask model. In this patent specification, rigorous simulation also encompasses approximation methods which take account of the three-dimensional structure of the mask model.

Carrying out the simulations as rigorous simulations has the advantage of a significantly higher accuracy in comparison for instance with so-called Kirchhoff simulation (a scalar approximation), in which all effects associated with the three-dimensionality of the mask are neglected and which becomes increasingly erroneous in particular for structures of the order of magnitude of the optical wavelength or in the case of polarization effects.

The scanner model describes changes in a mask model as a result of the imaging by the scanner. The scanner model comprises one or more parameters such as, for example: Numerical aperture, stop, Jones pupil, and polarization.

As explained in the introduction, the imaging behavior of a mask inspection microscope is highly adapted to the behavior of a scanner. During the recording of a measured aerial image by a mask inspection microscope, therefore, aerial images are obtained which to a good approximation are based on a mask model and a scanner model.

A scanner model can take account of further aspects which are not taken into account by the imaging behavior of a mask inspection microscope. In this regard, an imaging optical unit having a very high aperture on the wafer side is used for example during the imaging by a scanner on the wafer. This is not implemented in a mask inspection microscope during a magnified imaging onto a detector. The effect of this imaging on the aerial image can be taken into account by an extended scanner model. By way of example, polarization effects or apodization effects are taken into account in an extended scanner model.

Optical models can be applied to a mask design. In this way, a highly accurately simulated aerial image can be obtained by simulation.

The differences for assessing the parameters may be for example the dimensions of structure types.

A fast convergence of the parameters is made possible by an iterative method.

For example, the mask used in the method according to the invention can be embodied as a calibration mask. A calibration mask has known structure types. Each structure type present on a calibration mask can be present in different dimensions.

A wafer structure can be determined from an aerial image of the calibration mask by the application of a threshold value (as a simple resist model). To a good approximation, the dimensions from the mask design of the calibration mask can be used as dimensions for calibrating the aerial image or the wafer structure.

In one variant of the method, in order to obtain a highly accurate standard for the calibration, a calibration mask can be measured by a further method. By way of example, a Scanning Electron Microscope (SEM) can be used. Structure types of a calibration mask are for example "lines and spaces" or simple holes, referred to as "pinholes."

The mask used in the method according to the invention may be a mask to be examined. The method according to the invention makes it possible to determine the OPC model for a segment to be examined of said mask. If said segment is known, the simulated aerial image of the segment can be simulated on the basis of the mask design. The simulated aerial image and the measured aerial image can then be compared. Errors of the mask can then be deduced from differences.

In one variant of the method, a comparison of the wafer structures can be effected instead of or in addition to the comparison of the aerial images. In this case, the resist model is applied to each of the aerial images. If the scanner model is known, the mask model can be determined in a simple manner by use of this measure. In this regard, errors of the mask model can be identified. It is also possible to identify an inadequate mask design, which can then be correspondingly adapted.

If aerial images are known as a result of measurement or as a result of simulation, wafer structures can be determined from them by application of a resist model. This variant of the method can be used for determining a resist model. Firstly, a wafer structure is produced with respect to a calibration mask by illumination by use of a scanner. Said wafer structure is measured. The OPC model to be determined is adapted until the simulated wafer structure corresponds to the measured wafer structure, within the scope of predefined accuracy.

If the optical model is already known, then the resist model can be calibrated by use of this measure. A simulated aerial image is then firstly determined on the basis of the mask design and the optical model. The resist model is then determined therefrom, for example by use of an iterative method.

When a wafer exposure is carried out, fluctuations of some parameters can occur in practice. Said fluctuations can be taken into account during the creation and testing of a mask design. Examples of fluctuating parameters are for example the focus or the exposure. A so-called process window is defined by indication of those fluctuations which can still be afforded tolerance during the performance of a process. In order to determine a process window, a focus exposure matrix (FEM) can be determined, for example.

The invention encompasses a mask inspection microscope comprising a computing unit for carrying out the method.

Unless otherwise defined, all technical and scientific terms used herein have the same meaning as commonly understood by one of ordinary skill in the art to which this invention belongs. In case of conflict with patents or patent application publications incorporated herein by reference, the present specification, including definitions, will control.

DESCRIPTION OF DRAWINGS

The invention is described and explained in greater detail below on the basis of some selected exemplary embodiments and with reference to the drawings.

In the figures.

DETAILED DESCRIPTION

In order to carry out the method, aerial images are recorded by a mask inspection microscope 1. Said aerial images are referred to as measured aerial images.

Figure 1:
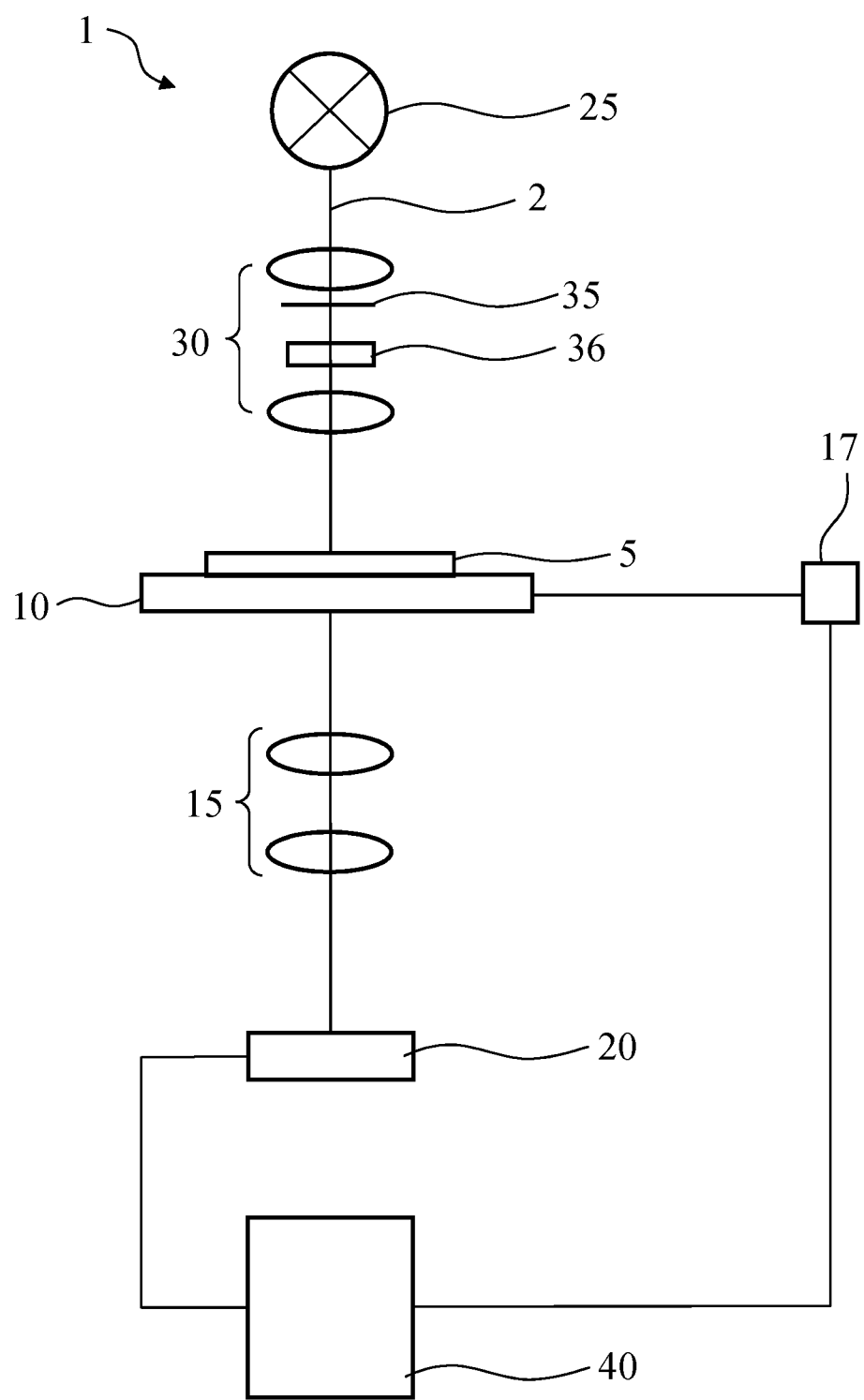
FIG. 1: shows the construction of a mask inspection microscope.

The construction of a mask inspection microscope 1 will be explained with reference to FIG. 1. The mask inspection microscope 1 has a mask holder 10, on which the mask 5 to be imaged lies, and a detector 20 embodied as a CCD chip or as CMOS chip. The mask holder 10 is movable in the X-Y-plane, i.e. perpendicularly to the optical axis. In this regard, the segment to be imaged of the mask 5 can be brought into the beam path. A light source 25 illuminates the mask 5 via an illumination optical unit 30. Illumination settings can be set by way of a pupil filter, which is arranged in the pupil plane 35, and a polarizer 36. During the recording of the aerial images, i.e. the projection of the mask 5, by use of the detector 20, use is made of illumination settings and polarization settings which are adapted to the structure and which are also used during the wafer exposure by use of a scanner. The wavelength of the illumination radiation is, e.g., also approximately 193 nm and corresponds to that of the scanner.

An aerial image of a segment of the mask 5 is generated via the imaging optical unit 15, with the optical axis 2, in the plane of the detector 20. The numerical aperture (NA) of the imaging optical unit 15 corresponds, on the mask side, to that of a scanner for the wafer exposure. The values for the NA are in the range of, e.g., 1.35 to 0.7 in the case of a 1:1 imaging by the scanner or in a range of, e.g., 0.3375 to 0.175 in the case of a reduction by the factor of four during the imaging by the scanner. For the purpose of focusing, the mask holder 10 is moved by drive 17 in the direction perpendicular to the X-Y plane, which is also referred to as the Z-direction, along the optical axis 2. Alternatively, for the purpose of focusing, the imaging optical unit 15 or the detector 20 is moved in the Z-direction by a drive (not illustrated in the drawing). The aerial image is read out by the computing unit 40, which is formed as a computer. The aerial image is initially present as a data structure in the main memory of the computer. Said data structure can be stored as a graphics file on the hard disk of the computer. The data structure or the graphics file is a two-dimensional matrix constructed from pixels. The intensities of the pixels are represented by numerical values for example in a range of 0 to 65535. The image field on the mask 5 is square, with an edge length of 10 μm, for example. The segment of the recorded partial structure is determined by the image field. The imaging scale is 450:1, for example.

Effects not taken into account by the mask inspection microscope described hitherto can occur during the imaging by a scanner. An imaging optical unit having a very high aperture is used during the imaging of a structure of a mask by a scanner onto a wafer. The effect of said imaging on the aerial image can be taken into account by an extended scanner model. By way of example, polarization effects or apodization effects are taken into account in an extended scanner model. The determination and application of an extended scanner model are disclosed in the published patent applications DE102005062237 and DE102005042496A1, and U.S. Pat. Nos. 7,626,689 and 7,961,297. The entire disclosure contents of DE102005062237, DE102005042496A1, U.S. Pat. Nos. 7,626,689, and 7,961,297 are incorporated by reference.

The simulation of an image is effected by commercially available software such as, for example, MicroSim on the basis of the structural stipulations of the mask, the mask design. The software is described for example in: M. Totzeck, "Numerical simulation of high-NA quantitative polarization microscopy and corresponding near-fields," Optik, 112 (2001) 381-390, MicroSim-Software, University of Stuttgart. The conditions of the imaging of the mask inspection microscope such as, for example, the numerical aperture, wavelength and degree of coherence of the illumination, etc. are taken into account in the simulation. Effects which lead to a distortion of the aerial image during the imaging of the mask by the mask inspection microscope, in particular proximity effects, are taken into account. With regard to proximity effects and with regard to the simulation of aerial images, reference is made to the publication: H. H. Hopkins: On the diffraction theory of optical images. Proceedings of the Royal Society of London. Series A, Mathematical and Physical Sciences, 217 (1130): 408-432, 1953.

The use of a three-dimensional mask model makes it possible to carry out a highly accurate determination of the simulated aerial images by use of rigorous simulation.

The mask model comprises a three-dimensional structure of the mask. The model comprises for example the thickness of the absorber on the mask substrate and variations of the thickness depending on the location on the mask. The mask model can also encompass side wall angles of the absorber. The mask model can also encompass the thickness of the mask substrate or the transmittance thereof or the refractive index thereof, and also location-dependent changes in these variables.

A rigorous simulation involves describing the diffraction of the light field at the mask taking account of the three-dimensionality of the mask, wherein in particular the three-dimensional geometry (in particular in the form of the mask model mentioned above) and also the concrete structure of the mask are taken into account. Furthermore, polarization effects (describable by Jones matrices) of the mask are also taken into account. Furthermore, the scanner model of the mask inspection microscope is taken into account. Upon implementation in commercial software, such as, for example, that from Mentor Graphics, approximations are also used in order to enable a faster calculation.

Using a calibration mask it is possible to determine an OPC model for an existing lithographic process. A calibration mask has for example structure types such as "lines and spaces" or simple holes, referred to as "pinholes". Each structure type present on a calibration mask can be present in different dimensions. During the calibration, i.e. in the calibrated OPC model, it is then possible to determine a correlation between the structure size on the mask and in the aerial image or on the wafer. This is important in particular for the smallest structures to be represented on a mask. These are referred to as critical dimensions, abbreviated to CD.

Figure 2:
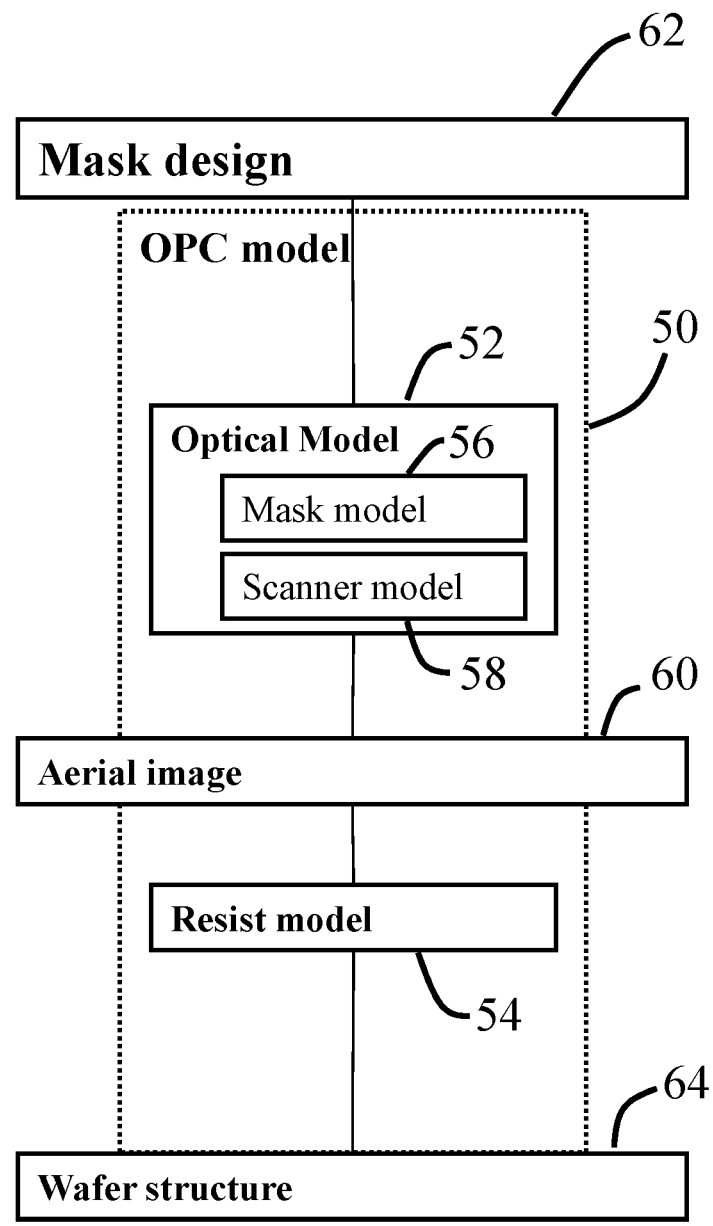
FIG. 2: shows a schematic diagram for elucidating the OPC model.

An overview of the application of an exemplary OPC model 50 is given in FIG. 2. The OPC model 50 includes an optical model 52 and a resist model 54. The optical model 52 includes a mask model 56 and a scanner model 58.

An aerial image of a segment of a calibration mask is recorded by a mask inspection microscope 1.

An aerial image 60 is simulated on the basis of the predefined mask design 62, the is mask model 56 and the scanner model 58. A rigorous simulation is preferably used in this case.

The optimization of the parameters of the OPC model 50 is preferably carried out iteratively. Parameters for the simulation of an aerial image are predefined. An aerial image 60 is then simulated. The measured aerial image and the simulated aerial image 60 are compared. The parameters are then changed, specifically such that a better correspondence between simulated aerial image 60 and measured aerial image is expected. If no information is present regarding what effects the change in a parameter has on the simulated aerial image 60, said parameter is changed experimentally in one direction. An aerial image 60 is then simulated again with the changed parameters. Upon the next comparison of measured aerial image and simulated aerial image 60, a decision is then taken as to whether the parameters are to be changed further in the same direction or in a different way. The iterative method is ended if the deviations fall below a predefined threshold value.

Examples of changes of parameters are the dimensions of the predefined mask structure. By way of example, critical dimensions (CD values) distributed over the mask are measured. Over these values, an average value is then formed, which is characteristic of the deviations. The root mean square can be determined here.

The iterative method is then carried out until the deviations of the structures fall below a threshold value. A further example is the comparison of intensity profiles of the aerial images.

In a first variant of the method, exclusively parameters of the mask model 56 are varied in order to determine further simulated aerial images 60.

In this variant, it is assumed that in the determination of the measured aerial images the scanner model 58 is implemented to a sufficiently good approximation by the above-described imaging behavior of the mask inspection microscope 1.

In a second variant, all parameters of the optical model 52 are varied in order to determine further simulated aerial images 60. This is advantageous if the scanner model 52 is not known exactly and the desired correspondence of simulated aerial image 60 and measured aerial image can be achieved only by variation of the parameters of the mask model 56. The following parameters of the scanner model 58 can be determined, for example: Numerical aperture, stop, Jones pupil, and polarization.

If the optical model 52 is known, a simulated aerial image 60 can be determined highly accurately from a predefined mask design 62 of a mask to be tested.

The following procedure is adopted in order to determine a resist model 54: An aerial image of a calibration mask is recorded by the mask inspection microscope 1. A resist model 54 is applied to the measured aerial image and a partly simulated wafer structure is thus obtained. Alternatively, a simulated aerial image 60 is determined on the basis of the mask design 62 of the mask to be tested and the optical OPC model 52 determined. The resist model 54 is applied to said simulated aerial image 60 and a simulated wafer structure 64 is thus obtained.

A wafer structure is produced by exposure of a wafer with the calibration mask by use of a scanner. Said wafer structure is measured by a CD-SEM device. The measured wafer structure is compared with the simulated or the partly simulated wafer structure 64. The adaption of the parameters of the resist model 54 is effected preferably iteratively as described above.

A number of possibilities are explained below for application of the OPC model 50 determined.

In order to test a mask, an aerial image of the segment to be tested is recorded. The resist model 54 determined is applied to the measured aerial image. The simulated wafer structure 64 thus obtained is compared with the wafer structure predefined for said segment. In a next step, the mask design 62 can be adapted such that a more accurate correspondence of the wafer structure to the stipulations is achieved. This optimization of the mask design 62 can be effected iteratively. In order not to produce a mask for every step of the optimization, a highly accurately simulated wafer structure 64 can be determined by application of the OPC model 50 to a changed mask design 62. This method is also referred to as mask biasing.

Not all of the parameters are constant during the performance of a real wafer exposure. In particular the focus position, the focus for short, and the exposure intensity, also referred to as exposure or dose, should expect fluctuations during a wafer exposure. Since the fluctuations of these parameters are critical for the correct production of the wafer structure, a minimum, optimum and maximum value are predefined for each of these parameters. In each case three values for the two parameters mentioned yield 9 combinations. A wafer structure can be determined in each case for all 9 combinations. These 9 structures are then referred to as a focus exposure matrix (FEM for short).

In order to determine these 9 wafer structures, firstly 9 corresponding aerial images are determined. Said aerial images can be recorded with stipulation of the respective focus and the respective exposure by the mask inspection microscope 1. The 9 aerial images can also be simulated on the basis of the mask design. This is possible with high accuracy if the optical model, as explained above, has been determined.

The resist model 54 is then applied to the 9 aerial images and the wafer structures are obtained.

The process of creating an FEM from aerial images involves firstly determining three aerial images with a different focus. The further images are determined from the measured aerial images after stipulation of varying values for the exposure, i.e. for the dose. In this case, for example, three threshold values can be predefined, but it is also possible to use a complex resist simulator.

Besides the use of OPC models 50, the joint optimization of illumination setting and mask structure can also be carried out. This technique is referred to as source mask optimization, SMO for short. The mask design 62 and the illumination setting are changed step by step. The effects on the resulting wafer structure 64 are then determined by the OPC model 50 being applied to the mask design 62. In further steps, the mask design 62 and the illumination setting (and also further parameters) can thus be optimized further.

In some implementations, the features described above related to processing of data (e.g., simulation of images, processing of mask models, processing of scanner models, optimization of the parameters of the OPC models) can be implemented by the computing unit 40, which can include one or more of digital electronic circuitry, computer hardware, firmware, and software. For example, some of the features can be implemented in a computer program product tangibly embodied in an information carrier, e.g., in a machine-readable storage device, for execution by a programmable processor; and method steps can be performed by a programmable processor executing a program of instructions to perform functions of the described implementations by operating on input data and generating output. Alternatively or in addition, the program instructions can be encoded on a propagated signal that is an artificially generated signal, e.g., a machine-generated electrical, optical, or electromagnetic signal, that is generated to encode information for transmission to suitable receiver apparatus for execution by a programmable processor.

The described features related to processing of data can be implemented advantageously in one or more computer programs that are executable on a programmable system including at least one programmable processor coupled to receive data and instructions from, and to transmit data and instructions to, a data storage system, an input device, and an output device. A computer program is a set of instructions that can be used, directly or indirectly, in a computer to perform a certain activity or bring about a certain result. A computer program can be written in any form of programming language (e.g., Fortran, C, C++, C #, Objective-C, Java, Python), including script, compiled, or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors or cores, of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, flash memory devices, and 3D XPoint™ memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a liquid crystal display (LCD) or an organic light emitting diode (OLED) monitor for displaying information to the user and a keyboard and a pointing device such as a mouse or a trackball, or a touch or voice interface by which the user can provide input to the computer.

A number of implementations have been described. Nevertheless, it will be understood that various modifications may be made. Accordingly, other implementations are within the scope of the following claims.

What is claimed is:

1. A method for determining an optical proximity correction (OPC) model comprising the following steps:
    recording an aerial image by use of a mask inspection microscope, wherein the aerial image comprises at least one segment of a mask;
    simulating a plurality of aerial images which comprise at least the segment, proceeding from a mask design and from predefined parameters of an optical model which is part of the OPC model, wherein the parameters of the optical model differ for each of the simulated aerial images of the plurality of aerial images;
    determining differences between the measured aerial image and the simulated aerial images; and
    determining those parameters of the optical model for which the differences between simulated aerial images and measured aerial image are the least.

2. The method according to claim 1, wherein the determination of parameters of the optical model is effected by way of an iteration,
    wherein in each case from the differences between a measured aerial image and an aerial image determined by simulation, a change in the parameters of the optical model is determined and these parameters of the optical model are chosen as parameters of the optical model of a following simulation.

3. The method according to claim 1, wherein the OPC model has at least one of the following models: optical model, resist model, wherein the optical model comprises at least one mask model and one scanner model.

4. The method according to claim 1, wherein a calibration mask is used as the mask.

5. The method according to claim 3, wherein in a first step parameters of the mask model are determined, wherein the parameters of the mask model comprise at least one of the following parameters: complex material refractive indices, the refractive index of the mask substrate, or thickness of the undercuts.

6. The method according to claim 3, wherein in a second step parameters of the scanner model are determined, wherein the parameters of the scanner model comprise at least one of the following parameters: Numerical aperture, stop, Jones pupil, polarization.

7. The method according to claim 1, comprising the following steps:
recording an aerial image of a segment of a mask;
simulating an aerial image on the basis of the mask design of the segment and of the OPC model determined; and
comparing the measured aerial image and the simulated aerial image.

8. The method according to claim 1, comprising the following steps:
determining a measured wafer image by carrying out a wafer exposure and recording an image of the exposed wafer;
determining a plurality of simulated wafer images on the basis of the measured aerial image, and of predefined parameters of the resist model, wherein the parameters of the resist model differ for each of the simulated wafer images of the plurality of wafer images;
determining differences between the measured and the simulated wafer images; and
determining the parameters of the resist model for which the differences between the simulated wafer images and the measured wafer image are the least.

9. The method according to claim 8, wherein the determination of parameters of the resist model is effected by way of an iteration,
wherein in each case from the differences between a measured wafer image and a wafer image determined by simulation, a change in the parameters of the resist model is determined and these parameters of the resist model are chosen as parameters of a following simulation.

10. The method according to claim 1, wherein a resist model is applied to a measured aerial image, wherein the structure obtained is compared with the structure desired on the wafer, wherein the mask structure is correspondingly adapted on the basis of the differences.

11. The method according to claim 1, wherein in each case a minimum, an optimum and a maximum value are predefined for focus and for exposure, and wafer structures are determined for all 9 pairs of focus and exposure values.

12. A microscope comprising:
a light source;
an imaging optical unit for imaging a substrate;
a detector for recording at least one aerial image of the substrate; and
a computing unit configured to execute instructions and carry out a process including:
processing data representative of an aerial image provided by the detector, wherein the aerial image comprises at least one segment of the substrate;
simulating a plurality of aerial images that include at least the segment, proceeding from a substrate design and from predefined parameters of an optical model which is part of an optical proximity correction (OPC) model, wherein the parameters of the optical model differ for each of the simulated aerial images of the plurality of aerial images;
determining differences between the measured aerial image and the simulated aerial images; and
determining those parameters of the optical model for which the differences between simulated aerial images and measured aerial image are the least.

13. The microscope of claim 12 in which the determination of parameters of the optical model is effected by way of an iteration, and
wherein in each case from the differences between a measured aerial image and an aerial image determined by simulation, a change in the parameters of the optical model is determined and these parameters of the optical model are chosen as parameters of the optical model of a following simulation.

14. The microscope of claim 12 in which the OPC model has at least one of the following models: optical model, resist model, and wherein the optical model comprises at least one mask model and one scanner model.

15. The microscope of claim 14, wherein in a first step parameters of the mask model are determined, wherein the parameters of the mask model comprise at least one of the following parameters: complex material refractive indices, the refractive index of the mask substrate, thickness of the undercuts.

16. The microscope of claim 14, wherein in a second step parameters of the scanner model are determined, wherein the parameters of the scanner model comprise at least one of the following parameters: Numerical aperture, stop, Jones pupil, polarization.

17. The microscope of claim 12 in which the process further comprises:
processing data representative of an aerial image of a segment of a mask;
simulating an aerial image on the basis of the mask design of the segment and of the OPC model determined; and
comparing the measured aerial image and the simulated aerial image.

18. The microscope of claim 12 in which the process further comprises:
processing data representative of a measured wafer image obtained by carrying out a wafer exposure and recording an image of the exposed wafer;
determining a plurality of simulated wafer images on the basis of the measured aerial image, and of predefined parameters of the resist model, wherein the parameters of the resist model differ for each of the simulated wafer images of the plurality of wafer images;
determining differences between the measured and the simulated wafer images; and
determining the parameters of the resist model for which the differences between the simulated wafer images and the measured wafer image are the least.

19. The microscope of claim 12 in which the process further includes applying a resist model is to a measured aerial image, comparing the structure obtained with the structure desired on the wafer, and adapting the mask structure on the basis of the differences.

20. The microscope of claim 12 in which the process further includes, in each case a minimum, an optimum and a maximum value are predefined for focus and for exposure, and wafer structures are determined for all 9 pairs of focus and exposure values.

21. The method of claim 3 in which in a first step parameters of the mask model are determined, wherein the parameters of the mask model comprise at least one of the following parameters: thickness of the absorber, side wall angle, corner rounding, change in the dimensions of structure features.

22. The method of claim 21 in which the change in the dimensions of structure features comprises at least one of changes in the line widths of structures or changes in the line end shortening.

23. The microscope of claim 14 in which in a first step parameters of the mask model are determined, wherein the parameters of the mask model comprise at least one of the following parameters: thickness of the absorber, side wall angle, corner rounding, change in the dimensions of structure features.

24. The microscope of claim 23 in which the change in the dimensions of structure features comprises at least one of changes in the line widths of structures or changes in the line end shortening.

* * * * *

UNITED STATES PATENT AND TRADEMARK OFFICE
CERTIFICATE OF CORRECTION

PATENT NO. : 10,539,865 B2
APPLICATION NO. : 15/715904
DATED : January 21, 2020
INVENTOR(S) : Holger Seitz et al.

Page 1 of 1

It is certified that error appears in the above-identified patent and that said Letters Patent is hereby corrected as shown below:

In the Specification

<u>Column 7</u>
Line 44, after "the" delete "is".

<u>Column 9</u>
Line 60, delete "C #" and insert -- C# --.

Signed and Sealed this
Thirty-first Day of March, 2020

Andrei Iancu
*Director of the United States Patent and Trademark Office*